(12) United States Patent
Katti et al.

(10) Patent No.: US 8,357,349 B2
(45) Date of Patent: Jan. 22, 2013

(54) COMPOUNDS FOR TREATMENT OF COPPER OVERLOAD

(75) Inventors: Kavita K. Katti, Columbia, MO (US); Kannan Raghuraman, Columbia, MO (US); Stan W. Casteel, Auxvasse, MO (US); Kattesh V. Katti, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 326 days.

(21) Appl. No.: 12/574,226

(22) Filed: Oct. 6, 2009

(65) Prior Publication Data

US 2010/0016583 A1     Jan. 21, 2010

Related U.S. Application Data

(60) Division of application No. 10/917,248, filed on Aug. 12, 2004, now Pat. No. 7,611,691, which is a continuation of application No. PCT/US03/05678, filed on Feb. 24, 2003.

(60) Provisional application No. 60/358,823, filed on Feb. 22, 2002.

(51) Int. Cl.
*A61K 51/00* (2006.01)
*A61M 36/14* (2006.01)
(52) U.S. Cl. ............ 424/1.77; 424/1.11; 424/1.65
(58) Field of Classification Search ........... 424/1.11, 424/1.65, 1.77, 1.69, 9.1; 549/200; 548/215
See application file for complete search history.

(56) References Cited

U.S. PATENT DOCUMENTS

| | | | |
|---|---|---|---|
| 3,578,708 A | 5/1971 | Carlson et al. | |
| 4,938,949 A | 7/1990 | Borch et al. | |
| 5,035,878 A | 7/1991 | Borch et al. | |
| 5,362,492 A | 11/1994 | Schuettler et al. | |
| 5,599,712 A | 2/1997 | Greenberger | |
| 5,637,315 A | 6/1997 | Zern et al. | |
| 5,647,315 A | 7/1997 | Saito | |
| 5,747,026 A | 5/1998 | Crapo et al. | |
| 5,848,290 A | 12/1998 | Yoshida et al. | |
| 5,948,386 A | 9/1999 | Katti et al. | |
| 5,994,339 A | 11/1999 | Crapo | |
| 6,030,611 A | 2/2000 | Gorecki et al. | |
| 6,040,611 A | 3/2000 | De Los Santos et al. | |
| 7,611,691 B2 * | 11/2009 | Katti et al. | ............ 424/1.77 |
| 2005/0054613 A1 | 3/2005 | Katti et al. | |

OTHER PUBLICATIONS

Berning et al, Journal of the American Chemical Socity, 1999, vol. 121, No. 8, pp. 1658-1664.*
"U.S. Appl. No. 10/917,248, Response filed Oct. 9, 2008 to Final Office Action mailed Apr. 17, 2008", 8 pgs.
"U.S. Appl. No. 10/917,248 Non-Final Office Action mailed Jan. 7, 2009", 12 pgs.
"U.S. Appl. No. 10/917,248 Response file Jan. 23, 2008 to Non-Final Office Action filed Jul. 23, 2008", 10 pgs.
"U.S. Appl. No. 10/917,248, Notice of Allowance mailed Jun. 25, 2009", 13 pgs.
"U.S. Appl. No. 10/917,248, Response filed May 7, 2009 to Non Final Office Action mailed Jan. 7, 2009", 8 pgs.
"U.S. Appl. No. 10/917,248, Advisory Action mailed Apr. 23, 2007", 3 pgs.
"U.S. Appl. No. 10/917,248, Final Office Action mailed Apr. 17, 2008", 7 pgs.
"U.S. Appl. No. 10/917,248, Final Office Action mailed Oct. 10, 2006", 11 pgs.
"U.S. Appl. No. 10/917,248, Final Office Action mailed Feb. 11, 2006", 8 pgs.
"U.S. Appl. No. 10/917,248, Non Final Office Action mailed Apr. 19, 2006", 6 pgs.
"U.S. Appl. No. 10/917,248, Non Final Office Action mailed Jul. 23, 2007", 9 pgs.
"U.S. Appl. No. 10/917,248, Response filed Jan. 20, 2006 to Restriction Requirement mailed Sep. 22, 2005", 9 pgs.
"U.S. Appl. No. 10/917,248, Response filed Feb. 26, 2007 to Final Office Action mailed Feb. 11, 2007", 9 pgs.
"U.S. Appl. No. 10/917,248, Response filed Jul. 19, 2006 to Non Final Office Action mailed Apr. 19, 2006", 6 pgs.
"U.S. Appl. No. 10/917,248, Restriction Requirement mailed Sep. 22, 2005", 8 pgs.
"Biochemicals, Organic Compounds and Diagnostic Reagents for Research", *Sigma Chemical Co. Catalog*, (1994), 85-88.
Berning, et al., *J. Am. Chem. Soc.*, 121, (1999), 1658-1664.
Dox, I. G, et al., "The Harper Collins Illustrated Medical Dictionary", (1993), 132.
Golub, T. R, et al., "Molecular Classification of Cancer : Class Discovery and Class Prediction by Gene Expression Monitoring", *Science*, vol. 286, (Oct. 15, 1999), 531-537.
Greene, T. W., *Protective Groups in Organic Synthesis*, Chapters 4, 5 & 6, John Wiley & Sons, Inc., New York, (1981), 114-217.

* cited by examiner

*Primary Examiner* — D L Jones
(74) *Attorney, Agent, or Firm* — Thompson Coburn LLP

(57) ABSTRACT

The present invention provides compounds, pharmaceutical compositions, and methods that can be used to treat pathologies that are due to copper overload or to the presence of reactive oxygen species.

6 Claims, 3 Drawing Sheets

COMPOUNDS FOR TREATMENT OF COPPER OVERLOAD

PRIORITY OF THE INVENTION

This application is a divisional of U.S. patent application Ser. No. 10/917,248 filed Aug. 12, 2004, which is a continuation under 35 U.S.C. 111(a) of International Application No. PCT/US03/05678 filed Feb. 24, 2003 and published in English as WO 03/072053 A2 on Sep. 4, 2003, which claims priority to U.S. Provisional Application Ser. No. 60/358,823, filed Feb. 22, 2002, which applications and publication are incorporated herein by reference.

BACKGROUND OF THE INVENTION

Copper overload is observed in various human conditions including cholestatic disorders, chronic ingestion of copper contaminated water, and in Wilson's disease. Similar conditions exist in veterinary medicine, including the susceptibility of sheep and various breeds of dogs, such as the Bedlington Terrier, to copper accumulation.

Wilson's disease is a genetic disorder that affects about one in 50,000 to 100,000 people worldwide. The disorder is due to abnormal changes (mutations) in a gene that is inherited as an autosomal recessive trait. The disease gene responsible for Wilson's disease, known as the ATP7B gene, is located on the long arm (q) of chromosome 13 (13q14.3). The protein encoded by this gene plays a role in the transport of copper (copper-transporting ATPase).

Wilson's disease, commonly known as hepatolenticular degeneration is a systemic disorder of copper metabolism. Patients with this disease suffer from copper accumulation in the liver. The liver eventually becomes overburdened from excessive copper storage and ultimately copper is released from the liver into other organs, particularly, the brain, eyes and the kidneys. Accumulation of copper in the liver causes acute or chronic inflammation of the liver (hepatitis) or severe liver disease due to progressive loss of liver function (cirrhosis). Common symptoms of copper accumulation in the liver include loss of appetite (anorexia), fatigue, weakness/weight loss, abdominal swelling/yellowish discoloration of the skin and eyes (jaundice). This disorder may also cause enlargement of the liver (hepatomegaly), spleen (splenomegaly) or in some cases, both (hepatosplenomegaly).

Neurologic disorders persist in individuals suffering from Wilson's disease. Neurologic symptoms include tremor of the head, arms/legs, slowness of movements (bradykinesia), particularly, those of the tongue, lips and jaw. Patients with Wilson's disease suffer from psychiatric problems. These symptoms include increasing agitation, irritability, drastic mood swings, depression accompanied by bizarre behaviors.

Therapy in individuals with copper overload pathologies such as Wilson's disease aims at efficacious removal of excessive copper from the body to prevent ongoing copper accumulation and deposition. This means that drug therapy must be continued throughout life. Lack of treatment or disruption of drug therapy often results in life threatening complications or irreversible organ damage. Current therapy for copper accumulation utilizes the chelating agent, D-penicillamine. D-penicillamine reduces copper toxicity by binding to copper in the body, making it water-soluble so it can be excreted in the urine.

Because D-penicillamine is a hydrolytic product of penicillin, it has been associated with the induction of hypersensitivity reactions. D-penicillamine reduces the amount of copper in the body, but it does not affect the increased levels of reactive oxygen species caused by the copper.

Reactive oxygen species and reactive nitrogen species (ROS/RNS), such as hydroxyl (OH.), peroxyl radicals (ROO.), superoxide anion ($O_2$.) and the peroxy nitrite anion (NO.), are constantly produced as a result of metabolic reactions in living systems. RNS and ROS that are associated with an increased amount of copper in the body attack critical biomolecules, such as lipids, proteins, nucleic acids, and the unsaturated fatty acids of biomembranes. These attacks result in lipid peroxidation and consequently cause the destruction of proteins and DNA. Various disorders and diseases in humans/animals such as cancers, brain disorders, platelet aggregation and atherosclerosis are associated with elevated levels of ROS/RNS.

Antioxidants are scavenging agents that typically react with ROS/RNS and effectively interrupt the propagation of new free radical species. While in vitro studies have shown that potent antioxidants protect against the oxidative stress induced by increased copper levels, the usefulness of antioxidants in copper toxicosis therapy is not well known. Therefore, a continuing need exists for effective therapies for copper overload conditions such as Wilson's disease.

SUMMARY OF THE INVENTION

The present invention provides a compound of formula (I):

$$[HO_2C\text{-}A\text{-}NH\text{—}CH_2]_3P \quad\quad (I)$$

or a pharmaceutically acceptable salt thereof, wherein each A is individually the residue of an amino acid. Preferably, each A is individually the residue of an α-amino acid, most preferably of a naturally occurring L-α-amino acid. This includes the alkylidenyl or substituted alkylidenyl residues derived from

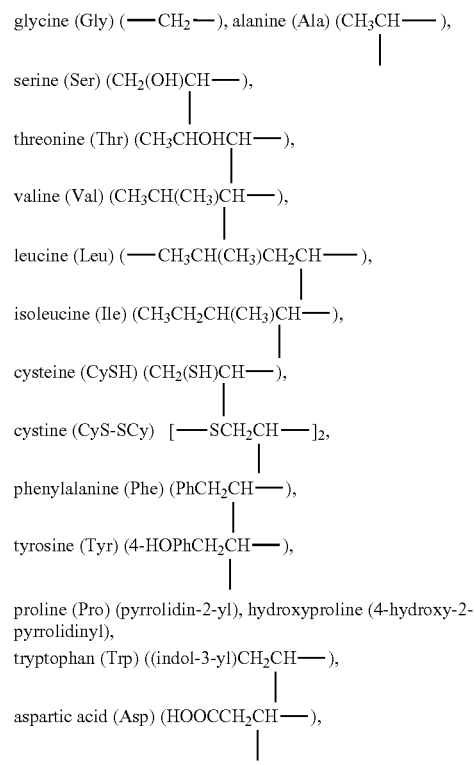

-continued

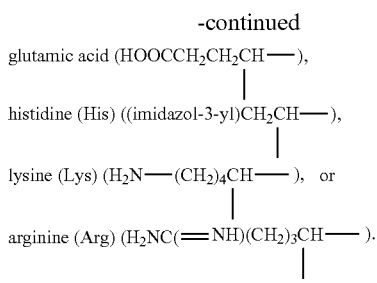

Free $CO_2H$, $NH_2$, OH, or SH groups on A groups can optionally be protected with suitable protecting groups (Z) such as tBoc, Cbz, acyl, amido, benzyl, silyl, hemiacetals, or ($C_1$-$C_4$) alkyl. Many protected and free, naturally occurring, synthetic or semisynthetic amino acids useful in the synthesis of compounds of formula (I) are commercially available. See, e.g., *Biochemicals Organic Compounds and Diagnostic Reagents for Research*, Sigma Chemical Co. Catalog (1994) at pages 85-88.

Preferably at least two of the A moieties are identical, most preferably all three A moieties are derived from the same amino acid, such as alanine, glycine, valine, leucine, isoleucine and the like.

The compound of formula I where A is

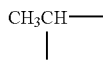

is named thpalanine (THPAL):

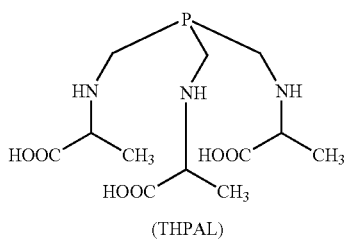 [SMILES: CC(NCP(CNC(C)C(=O)O)CNC(C)C(=O)O)C(=O)O]

(THPAL)

Although the compounds of formula (I) can be administered as free acids, pharmaceutically acceptable salts of said compounds can be employed, either as intermediates in the preparation of the free acids, to stabilize the free acids, or to enhance their solubility in aqueous media or in other solvents. Such salts include non-toxic quaternary amine salts and alkali metal salts, such as ammonium, sodium, potassium, hydroxyethylammonium, and the like.

The compounds of the invention provide therapeutic agents that possess the dual functions of being antioxidants and powerful chelators of copper ($Cu^{+2}$), in vitro and in vivo. Therefore, the present invention also provides a therapeutic method for the treatment of a copper overload pathology (copper toxicosis or copper storage disease) comprising administering to a mammal, such as a human or domestic animal, afflicted with such a pathology, an effective amount of a compound of formula (I), such as a tris[carboxy-A-NH—$CH_2$]$_3$P compound, wherein A is the residue of a naturally occurring or synthetic amino acid.

The present invention further provides a pharmaceutically acceptable composition comprising an effective amount of a compound of formula (I), such as THPAL, in combination with a pharmaceutically acceptable carrier, such as a liquid vehicle. The composition is preferably adapted to parenteral administration, to a mammal in need of such therapy, e.g., by intravenous administration.

The present invention also includes compounds of formula (I) that are useful as intermediates in the preparation of other compounds of formula (I), such as compounds wherein 1-3 $CO_2H$ are replaced by $CO_2R$ wherein R is ($C_1$-$C_4$)alkyl, benzyl, $NH_2$, mono- or disubstituted amino, and the like. The invention also includes compounds of formula (I) wherein two $CO_2H$ groups have formed an anhydro group [C(O)OC(O)]. The invention also includes compounds of formula (I) wherein 1-3 NH groups have been replaced by N(R) wherein R is an amino protecting group, ($C_1$-$C_4$)alkyl, benzyl, and others disclosed hereinabove, as known in the art of peptide synthesis. Thus, the present invention also provides compounds of formula (III):

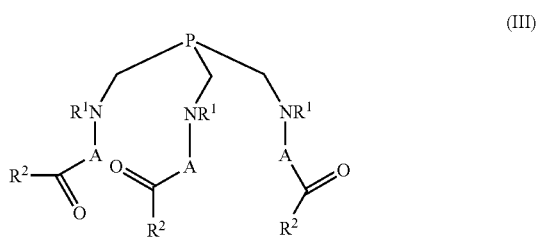

(III)

wherein:
each $R^1$ is independently hydrogen, ($C_1$-$C_6$)alkyl, or an amino protecting group;
each $R^2$ is independently $OR^c$ or $NR^aR^b$; or two $R^2$ groups together with the atoms to which they are attached for an anhydride;
each A is independently the residue of an amino acid;
each $R^a$ and $R^b$ is independently hydrogen, ($C_1$-$C_6$)alkyl, ($C_1$-$C_6$)alkanoyl, phenyl, or benzyl; or $R^a$ and $R^b$ together with the nitrogen to which they are attached form a pyrrolidino, piperidino, morpholino, or thiomorpholino ring; and
$R^c$ is ($C_1$-$C_6$)alkyl, phenyl, benzyl, or a carboxy protecting group. In one embodiment, the invention provides a compound of formula (III) wherein at least one of $R^1$ or $R^c$ is other than hydrogen. The invention also provides a method for preparing a compound of formula (I) comprising deprotecting a corresponding compound of formula (III) wherein at least one of $R^1$ or $R^c$ is a protecting group.

The present compounds also can be used to concentrate copper ions from water, in refining or decontamination processes.

The invention also provides synthetic intermediates and processes disclosed herein that are useful for preparing compounds of the invention.

DETAILED DESCRIPTION OF THE INVENTION

Figure 1:
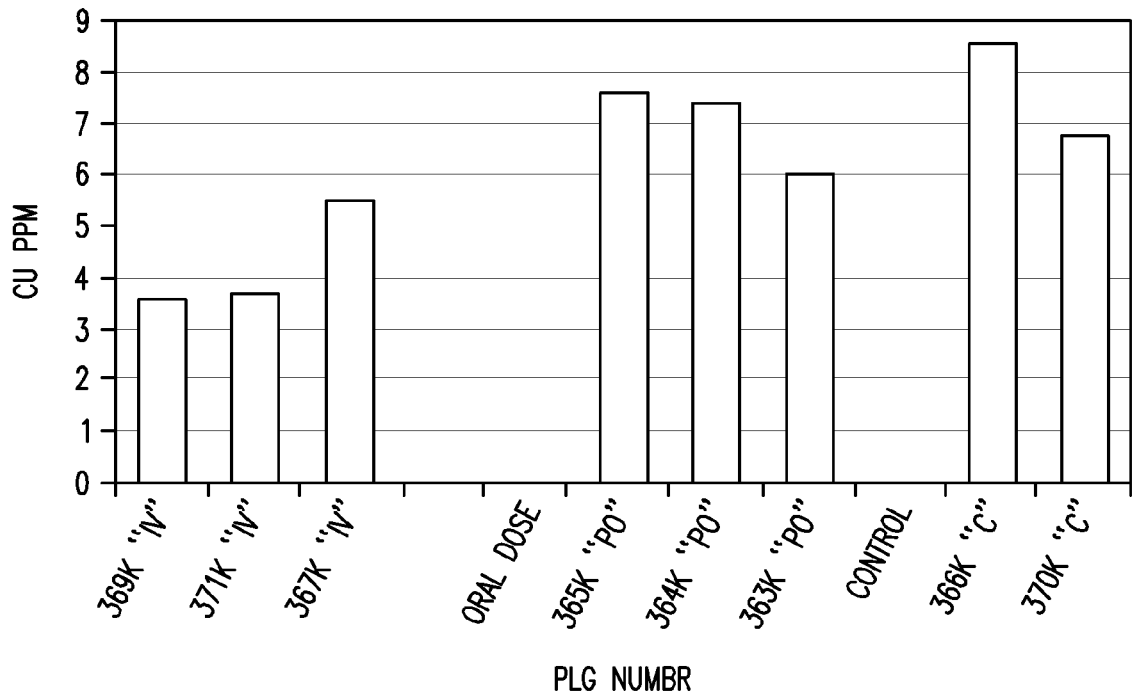
FIG. 1 is a graph depicted reduction of copper (Cu) in kidneys of swine by THPAL.

The presence of trivalent phosphorus and multicarboxylates in the compounds of formula (I) is significant because these functional groups provide antioxidant properties to this new chemotherapeutic drug. Therefore, compounds of formula (I), such as thpalanine, that are able to serve the dual purposes of copper (Cu) chelation and prevention of oxidative damage should be more effective in treating copper toxicosis than current therapeutic approaches. Thus, compounds of formula (I) can be used in the treatment of copper toxicosis and copper storage diseases in both human and veterinary medicine. As shown in Example 3, thpalanine is effective as a drug for treating a model of Wilson's disease.

Copper overload is observed in various human conditions including cholestatic disorders, chronic ingestion of copper-contaminated water, and in Menkes and Wilson's disease. Similar conditions exist in veterinary medicine, including the susceptibility of sheep and various breeds of dogs, such as the Bedlington Terrier, to copper accumulation. Current therapy for copper accumulation utilizes the chelating agent, D-penicillamine. D-penicillamine reduces copper toxicity by binding to copper in the body, making it water-soluble so it can be excreted in the urine. Because D-penicillamine is a hydrolytic product of penicillin, it has been associated with the induction of hypersensitivity reactions. D-penicillamine reduces the amount of copper in the body, but it does not affect the increased levels of reactive oxygen species caused by the copper. The increased amounts of oxygen radicals associated with copper accumulation are responsible for damage to critical biomolecules such as lipids, proteins and nucleic acids.

The current invention provides new therapeutic agents that serve the dual functions of being antioxidants and powerful chelators of copper. The results of in vivo and in vitro studies on this agent have demonstrated that these new agents can be effective in the treatment of copper toxicosis and copper storage diseases in both human and veterinary medicine.

As demonstrated in Example 1, compounds of formula (I) can be prepared from amino acid(s) and tris(hydroxymethyl) phosphine, by combining the amino acid(s) and the phosphine in aqueous solution, followed by removal of the water in vacuo to yield the product. If amino acids comprise functional groups such as additional $CO_2H$, or groups such as OH that might compete for reaction with the phosphine OH, suitable selective protecting groups such as tris(alkyl)silyl, THP, acyl, EtOEt or benzyl can be employed, that can be removed under mild conditions following the esterification step. Other useful amine and carboxyl protecting groups are disclosed in T. Greene et al., *Protecting Group in Organic Synthesis*, Wiley, N.Y. (2d ed. 1991).

The present invention includes a method to reduce oxidative stress in a subject as well as a method to alleviate a deleterious condition in a subject where the condition is associated with the production of an oxidant. Examples of such conditions include, but are not limited to, aberrant smooth muscle disorder, liver disease, proliferation of cancer cells, inflammation in cancer patients receiving radiotherapy, inflammatory diseases (arthritis, vasculitis, glomerulonephritis, systemic lupus erythematosus, and adult respiratory distress syndrome), ischemic diseases (heart disease, stroke, intestinal ischemia, and reperfusion injury), hemochromatosis, acquired immunodeficiency syndrome, emphysema, organ transplantation, gastric ulcers, hypertension, preeclampsia, neurological diseases (multiple sclerosis, Alzheimer's disease, Parkinson's disease, amyotrophic lateral sclerosis, and muscular dystrophy) alcoholism, and smoking-related diseases.

Cells in which oxidative stress is deleterious include, but are not limited to, endothelial, interstitial, epithelial, muscle (smooth, skeletal or cardiac), phagocytic (including neutrophils and macrophages), white blood cells, dendritic, connective tissue and nervous system cells. Effected tissues include but are not limited to muscle, nervous, skin, glandular, mesenchymal, splenic, sclerous, epithelial and endothelial tissues.

The literature as well as numerous patents describe the use of antioxidants to treat various conditions induced or caused by oxidative stress. Examples of these patents include U.S. Pat. Nos. 5,362,492; 5,599,712; 5,637,315; 5,647,315; 5,747,026; 5,848,290; 5,994,339; 6,030,611 and 6,040,611.

Examples 5-8 demonstrate that representative compounds of formula I can be used to as antioxidants to reduce oxidative stress. The antioxidant properties of compounds of formula I, particularly THPAL, $P(CH_2NHCH(CH_3)COOH)_3$, were tested under various different in vitro conditions. The stability of THPAL in bovine serum albumin (BSA)(Example 5), the ability of molecular oxygen to oxidize THPAL (Example 6), the ability of gaseous hydrogen peroxide to exidize THPAL (Example 7), and the ability of a 35% aqueous $H_2O_2$ solution to oxidize THPAL (Example 8) was tested. The results from these tests demonstrate that THPAL is not oxidized in solutions of BSA, by atmospheric oxygen or oxygen dissolved in water at reflux temperatures at physiological pH. However, the interaction of THPAL with oxygen radicals generated by peroxide, demonstrated complete oxidation of THPAL to the corresponding oxide, $O=P(CH_2NHCH(CH_3)COOH)_3$ (Scheme I).

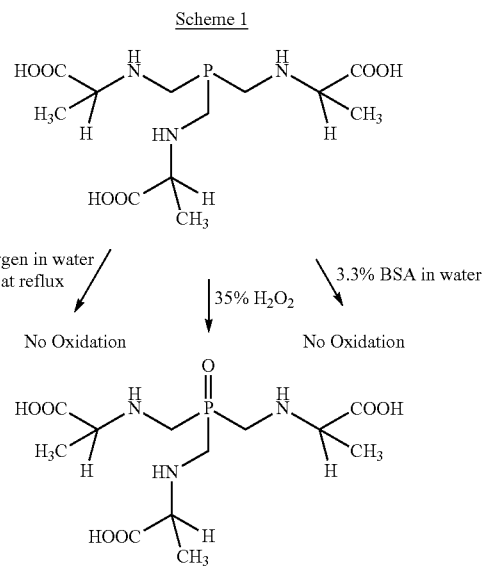

Scheme 1

Accordingly, the results show that the compounds of formula I can be used as antioxidants to treat diseases and disorders in humans and animals that are associated with increased amounts of reactive oxygen species (ROS). For example, Wilsons disease produces increased levels of ROS because of the high levels of copper. Thus, the compounds of formula I are superior to the current treatment schemes for Wilsons disease because the currently available therapy for Wilsons disease involves use of pencillamine which does not reduce or eliminate ROS in the body. Therefore, compounds of formula I, particularly THPAL, are through to be very useful for clinical application due to their dual properties as copper chelators and non-toxic antioxidants.

Administration and Dosages

While it is possible that, for use in therapy, the compound(s) of formula (I) may be administered as the pure chemicals, for example, as by inhalation of a fine powder via an insufflator, it is preferable to present the active ingredient as a pharmaceutical formulation. The invention thus further provides a pharmaceutical formulation comprising a compound of formula (I) and/or a pharmaceutically acceptable salt thereof, together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof, such as a human patient or domestic animal.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical formulations suitable for oral administration may be presented as discrete unit dosage forms such as hard or soft gelatin capsules, cachets or tablets each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dose form in ampules, pre-filled syringes, small volume infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

When desired, the above-described formulations can be adapted to give sustained release of the active ingredient employed, e.g., by combination with certain hydrophilic polymer matrices, e.g., comprising natural gels, synthetic polymer gels or mixtures thereof.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the compounds of the invention may be administered via a liquid spray, such as via a plastic bottle atomizer. Typical of these are the Mistometer® (Wintrop) and the Medihaler® (Riker).

Usually, the active substance will comprise between about 0.05 and 99%, or between 0.1 and 95% by weight of the resulting pharmaceutical unit dosage form, for example, between about 0.5 and 20% of preparation intended for injection or infusion and between 0.1 and 50% of preparation, such as tablets or capsules, intended for oral administration.

Doses of a given compound of formula (I) which are effective to counteract the deleterious effects of copper ($Cu^{+1}$, $Cu^{+2}$), including copper salts will necessarily vary depending upon the age, weight and condition of the mammal, e.g., human or dog, to be treated, as well as upon the type and severity of the condition to be treated. For example, daily doses of about 0.5-100 mg/kg, e.g., 1-50 mg/kg, in single or divided doses, can be employed. The effective doses can be extrapolated, to some extent, from the swine data disclosed hereinbelow, by methods known to the art for extrapolation of animal dosing data to humans. For example, see U.S. Pat. Nos. 5,035,878 and 4,938,949.

The invention also provides a method for preparing a copper complex of formula II (below) comprising contacting a corresponding compound of formula I with a suitable copper ion source.

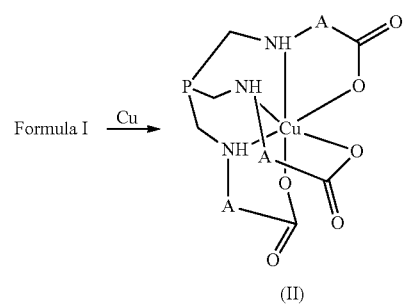

(II)

The invention also provides a copper complex of formula II wherein A has any of the values defined herein.

The invention will now be illustrated by the following non-limiting examples.

Example 1

Synthesis of 2-[({Bis-[(1-carboxy-ethylamino)-methyl]-phosphanyl}-methyl)-amino]-propionic acid (THP-Alanine THPAL or "Thpalanine")

As shown in Scheme II, alanine (2.15 g, 24.19 mmol) in 25 mL of distilled water was added to tris(hydroxymethyl)phosphine (1.00 g, 8.06 mmol) in water (15 mL) at 25° C. The reaction was stirred under dry nitrogen for one hour. The solvent was removed in vacuo to obtain a solid. The residue was washed in methanol (3×15 mL) and dried in vacuo to yield the analytically pure compound (THPAL) in 95% yield (2.58 g) as a white solid; ESI/MS calcd for $C_{12}H_{24}N_3O_6P$ [M+H]$^+$ 337.31, found 338.20; Anal. (calcd) for $C_{12}H_{24}N_3O_6P$: C, 42.73, H, 7.17. N 12.46. Found: C, 43.21, H, 7.54, N, 11.76; $^1$H NMR (D$_2$O, 300 MHz): δ 1.37 (d, 9H, —CH(CH$_3$), 3.47 (d, 6H, P—(CH$_2$)), 3.65 (q, 3H, —CH(CH$_3$);$^{13}$C NMR (D$_2$O, 75 MHz): δ 14.84 (s, —CH(CH$_3$), 42.65 (d, P—CH$_2$, $^1J_{P-C}$=12.83 Hz), 59.36 (d, CH(CH$_3$),$^3J_{P-C}$=5.30 Hz), 174.09 (s, —COOH); $^{31}$P{$^1$H} NMR (D$_2$O, 121.5 MHz): −39.50 (s).

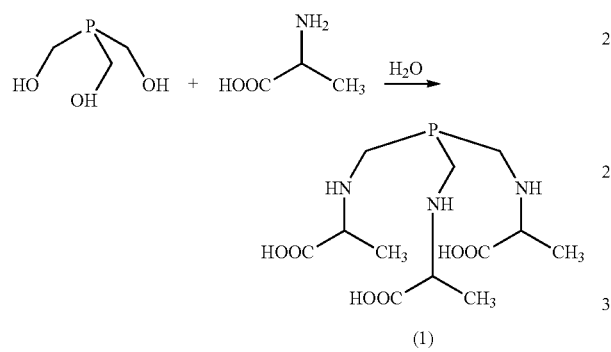

Scheme II (1)

Example 2

Synthesis of THP-Amino Acids

Following the general procedure of Example 1, but substituting, respectively, glycine, serine, threonine, valine, leucine, isoleucine, cysteine, cystine, phenylalanine, tyrosine, proline, hydroxyproline, tryptophan, aspartic acid, glutamic acid, histidine, lysine or arginine for valine afforded corresponding compounds [HO$_2$C-A-NHCH$_2$]$_3$P wherein A is the residue of the α-amino acid, as depicted above.

Example 3

Synthesis of Cu Complex of THP-Alanine

THPAL (1.00 g, 2.96 mmol) in 10 mL of distilled water was added dropwise to CuSO$_4$ (0.47 g, 2.96 mmol) in water (20 mL) at 25° C. Color change of the reaction mixture from light blue to deep blue was immediately observed. The reaction was stirred for 30 minutes. The solvent was removed to obtain a blue solid. The residue was washed with cold water (2×3 mL) and dried in vacuo to yield the copper compound (2) in 90% yield as a blue solid; ESI/MS calcd for [M+H]$^+$ 397.83, found 399.33; satisfactory elemental analysis data was also obtained.

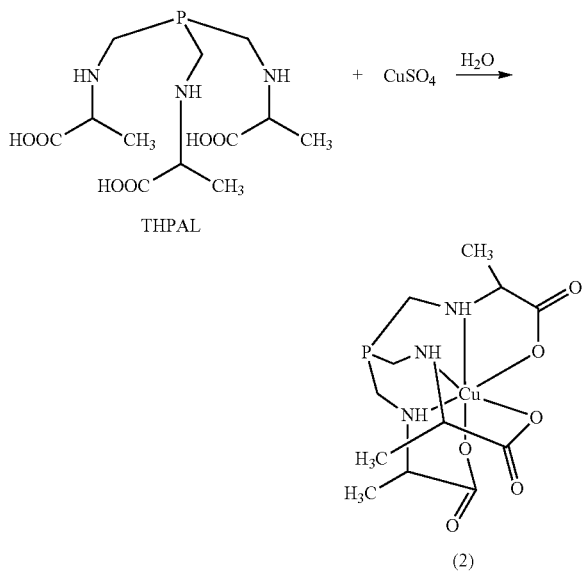

(2)

Example 4

Reduction of Copper Levels in Swine

Eight weanling pigs weighing 10-12 kg were randomly assigned to one of three groups, receiving no thpalanine (N=2), thpalanine via gavage (N=3) or thpalanine intravenously (N=3). All eight pigs underwent 21 consecutive days of oral Cu loading with 10 mg of Cu from copper sulfate per kg of body weight twice daily. Loading was determined by protocol in *Mineral Tolerance of Domestic Animals*. Pigs also received 10 mg/kg body weight of Cu in their diet. After 21 days dosing with copper sulfate was discontinued. Thpalanine was given to the two drug-treated groups beginning two days following the end of Cu loading. Each of the thpalanine treatment groups (oral and intravenous) received 15 mg thpalanine per kg body weight twice daily for three consecutive days. Four 24 hour urine collections were done to determine urinary Cu excretion beginning 24 hours prior to thpalanine treatment.

Following day 3 of treatment, the pigs were euthanized and a sample of liver/kidney were collected and stored at −10° F. until copper analyses. Statistical analysis was performed using ANOVA. Multiple pairwise comparisons were made using the Tukey test and statistical significance was set at P<0.05. The results of these studies demonstrated that liver and kidney copper levels were not elevated but were, in fact, within normal limits reported by *Mineral Levels in Animal Health*. In fact, copper levels in swine kidneys were significantly reduced in the intravenously administered thpalanine treatment group (FIG. 1). Based on clinical observations, rate of gain, and gross necropsy, the pigs showed no adverse effects due to the thpalanine.

Example 5

Stability of THPAL in Bovine Serum Albumin (BSA)

50 mg of BSA (3.3%) was dissolved in 1.5 ml of water. 30 mg of THPAL (0.06 M) was added to this to obtain a clear solution. The measurements of stable (or unoxidized) forms of THPAL in BSA were performed using $^{31}$P NMR spectroscopy. The $^{31}$P NMR resonance of THPAL is very sensitive to alterations on the back bone structure. The temperature of the mixture of THPAL and BSA in water was maintained at 9-12° C.

Figure 2:
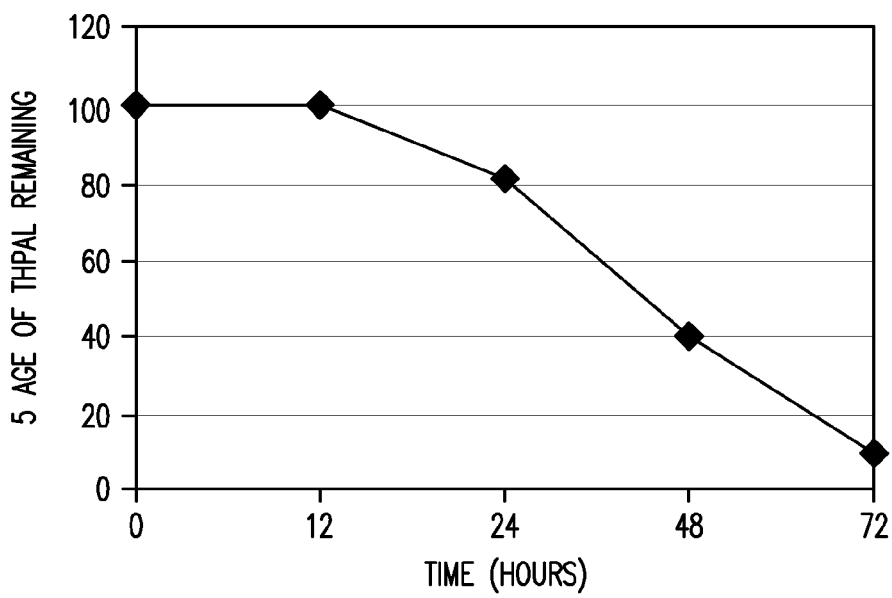
FIG. 2 shows the percentage of undecomposed THPAL in BSA solution with time.
Figure 3:
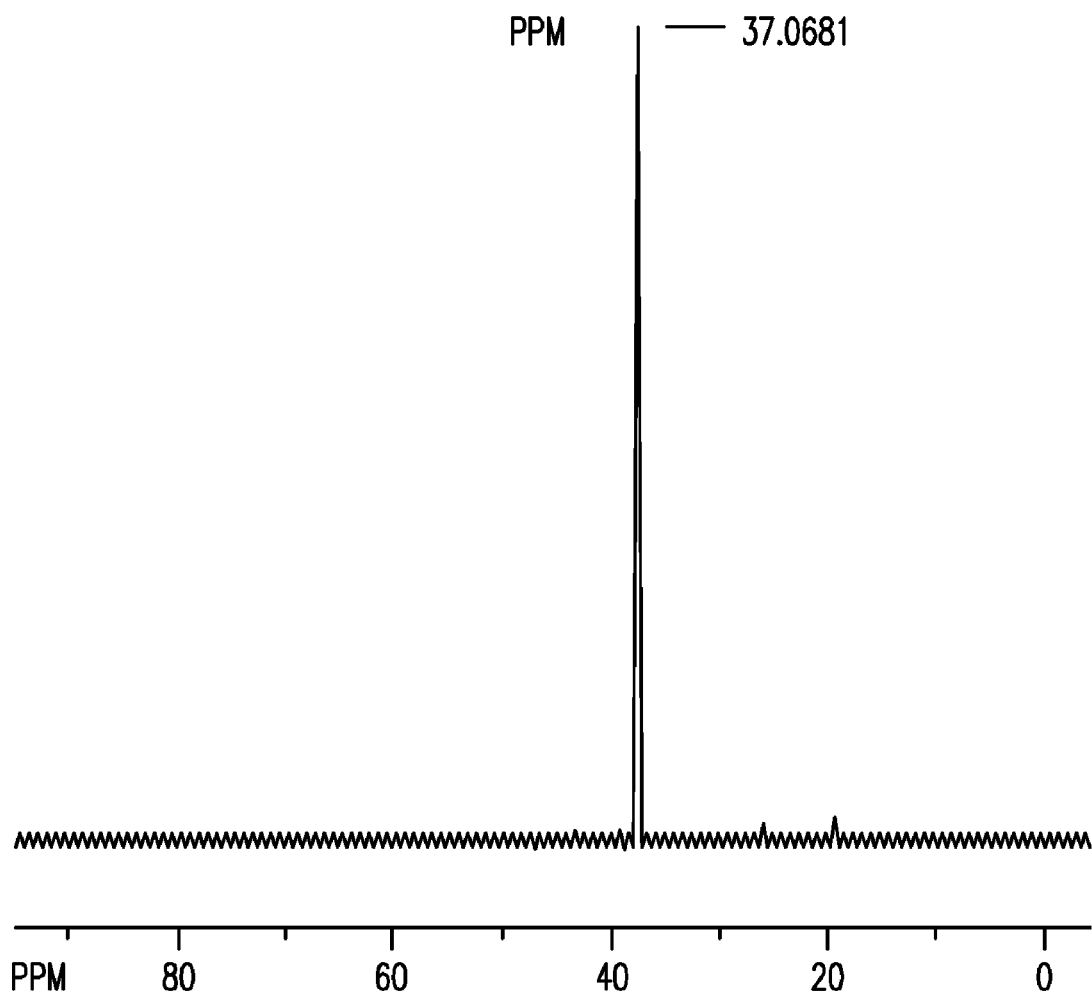
FIG. 3 shows the $^{31}P$ NMR ($D_2O$) spectrum of P(O)($CH_2NHCH(CH_3)COOH)_3$.
Figure 4:
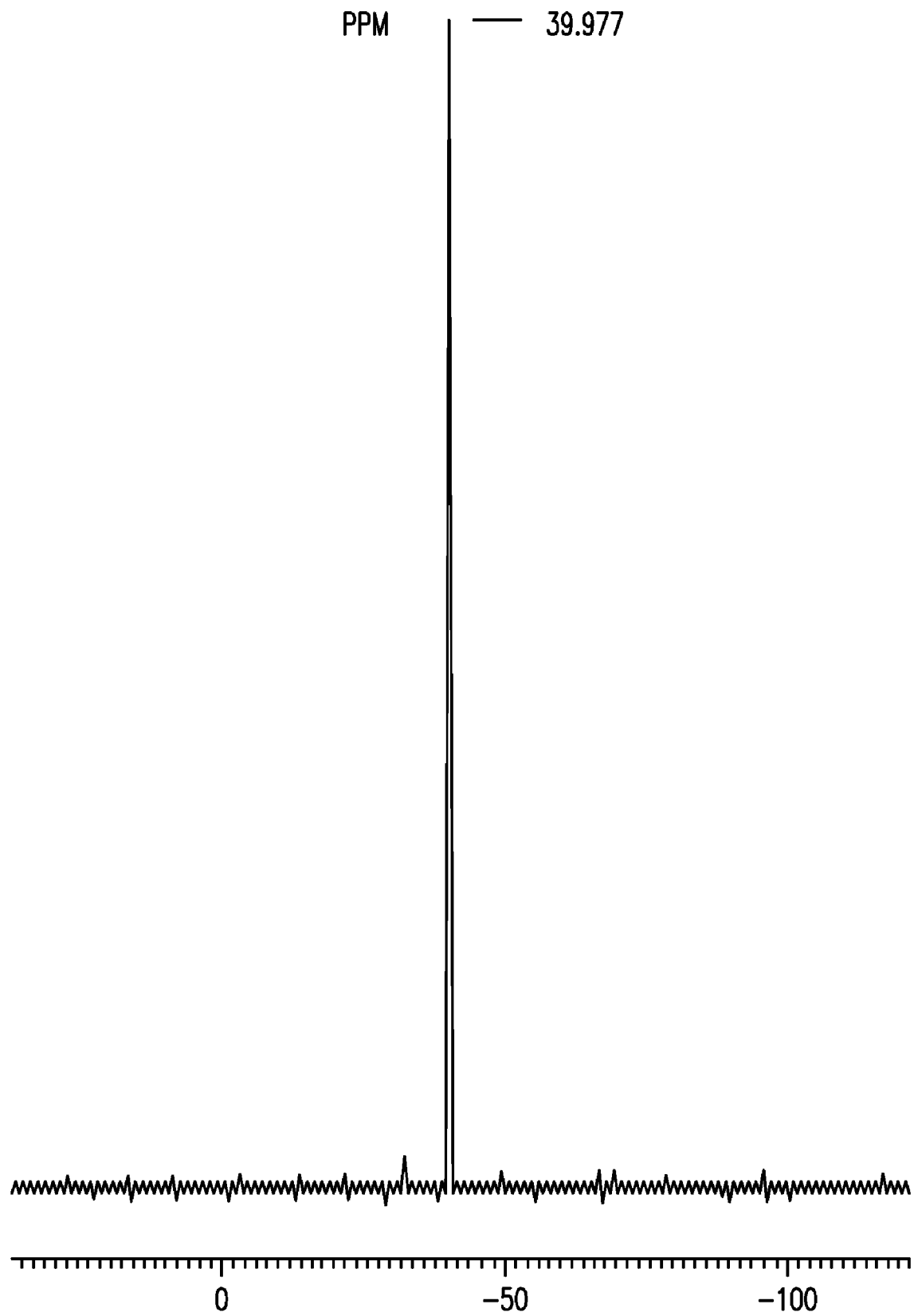
FIG. 4 shows the $^{31}P$ NMR ($D_2O$) spectrum of $P(CH_2NHCH(CH_3)COOH)_3$.

The percentage of THPAL remaining with time was plotted as shown in FIG. 2. There was no detectable change in the $^{31}$P NMR resonance until 12-15 hours after mixing the THPAL and BSA. After 24 hours, about 20% THPAL was transferred to uncharacterized compound. The absence of $^{31}$P NMR resonance in the positive region indicated that the THPAL remained unoxidized even after 72 hours (see FIGS. 3 and 4 for $^{31}$P NMR spectra of THPAL and oxidized THPAL).

The results confirmed that THPAL is stable in BSA solutions. The $^{31}$P NMR study confirmed the oxidative stability (no oxidation even after five days) of THPAL in BSA solution. This result showed that compounds of formula I, THPAL for example, can be administered in vivo as an antioxidant drug in humans and animals.

Example 6

Attempted Oxidation of THPAL with Molecular Oxygen

THPAL (0.5 g, 0.014 mmol) was dissolved in aerated water (25 ml). The mixture was refluxed for several hours under air. $^{31}$P NMR of the reaction mixture did not show any oxidation or detectable decomposition Example 7

Oxidation of THPAL Using Gaseous Hydrogen Peroxide

THPAL (0.05 g, 0.0014 mmol) was dissolved in water (1.0 ml). This solution was exposed to hydrogen peroxide vapors for 12-24 hours. Complete conversion to O=P(CH$_2$NHCH(CH$_3$)COOH)$_3$ was observed after two days. Micro crystalline O=P(CH$_2$NHCH(CH$_3$)COOH)$_3$ was obtained.

Example 8

Oxidation of THPAL by 35% Aqueous H$_2$O$_2$

Hydrogen peroxide (0.2 ml, 35%, 0.014 mmol) was added dropwise to a solution of THPAL (0.5 g, 0.014 mmol) in water at room temperature. The reaction mixture was stirred at room temperature for one hour. The solvent was then removed under reduced pressure. The crude product was washed with methanol (5×4 ml), and then characterized as pure O=P(CH$_2$NHCH(CH$_3$)—COOH)$_3$ by NMR spectroscopy. $^{31}$P{$^1$H} NMR (D$_2$O): 37.07 (s); $^1$H NMR (D$_2$O): 1.60 (d, CH$_3$, 9H), 3.96-3.89 (m, CH$_2$ and CH, 9H); $^{13}$C NMR (D$_2$O): 42.9 (d, P—CH$_2$, J$_{C-P}$=70.05 Hz), 59.6 (d, NH—CH, $^2$J$_{C-P}$=8.25 Hz), 15.59 (s, CH3), 175.15 (s, COOH).

Example 9

Antioxidant Properties of THPAL

Oxygen radical absorbance capacity (ORAC) and Hydroxy radical absorbance capacity (HORAC) analysis indicated that THPAL possesses remarkable antioxidant properties (Table 1). NORAC assays of THPAL were used to demonstrate high efficacy for scavenging RNS, indicating its potential as a new generation antioxidant (Table 1). The NORAC value of 18.8 μmolTE/g found for THPAL (Table 1) is among the highest ever reported for antioxidant drugs. The non-toxic nature of THPAL coupled with its excellent antioxidant capability indicates that THPAL can serve as an effective antioxidant.

TABLE 1

| | ORAC/HORAC/NORAC data for THPAL | | |
|---|---|---|---|
| Sample ID | ORAC$_{hydroFL}$* (μmoleTE/g) | HORAC+ (mgGAE/g) | NORAC^ (μmoleTE/g) |
| THPAL | 31 | Not Detectable | 18.81 |

*The ORAC$_{FL}$ analysis utilized Fluorescein as the fluorescent probe and provides a measure of the scavenging capacity of antioxidants against the peroxyl radical. The peroxyl radical is one of the most common reactive oxygen species (ROS) found in the body. ORAC$_{hydro}$ reflects water-soluble antioxidant capacity.
Trolox, a water-soluble Vitamin E analog, was used as the calibration standard and the ORAC result is expressed as micromole Trolox equivalent (TE) per gram.
+Gallic Acid was used as the calibration standard and the HORAC result is expressed as mg Gallic Acid equivalent(GAE) per gram.
^Trolox was used as the calibration standard and the NORAC result is expressed as μmole Trolox equivalent (TE) per gram.
Acronyms: ORAC: Oxygen Radical Absorbance Capacity; HORAC: Hydroxyl Radical Absorbance Capacity; NORAC: Nitricoxide Radical Absorbance Capacity; ROS: Reactive Oxygen Species; RNS: Reactive Nitrogen Species All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (II)

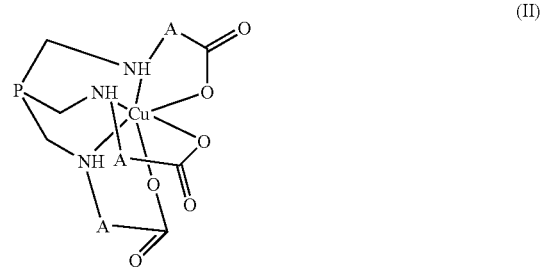

wherein each A is an independently selected residue of an amino acid, wherein the residue is the portion of the amino acid that is not an amine group nor a carboxyl group.

2. The compound of claim 1, wherein each A is the residue of an α-amino acid.

3. The compound of claim 1, wherein each A is the residue of a naturally occurring L-amino acid.

4. The compound of claim 1, wherein each A is the residue of the same amino acid.

5. The compound of claim 1, wherein A is an alkylidenyl or a substituted alkylidenyl residue of glycine, alanine, serine, threonine, valine, leucine, isoleucine, phenylalanine or tryptophan.

6. The compound of claim 1, wherein A is methylene or CH$_3$CH—.

\* \* \* \* \*